United States Patent

Nakamura

[19]

[11] Patent Number: 6,050,530
[45] Date of Patent: Apr. 18, 2000

[54] AUTOMATIC BALANCING MECHANISM FOR MEDICAL STAND APPARATUS

[75] Inventor: Katsushige Nakamura, Tokyo, Japan

[73] Assignee: Mitaka Kohki Co., Ltd., Tokyo, Japan

[21] Appl. No.: 08/769,349

[22] Filed: Dec. 19, 1996

[30] Foreign Application Priority Data

Dec. 28, 1995 [JP] Japan ................................ 7-343708

[51] Int. Cl.$^7$ .............................................. G02B 21/00
[52] U.S. Cl. .............................. 248/123.2; 248/280.11; 248/781.11; 248/292.11; 359/384
[58] Field of Search .................... 248/123.11, 123.2, 248/280.11, 281.11, 292.11; 359/384

[56] References Cited

U.S. PATENT DOCUMENTS

| 3,891,301 | 6/1975 | Heller | 359/384 |
| 4,339,100 | 7/1982 | Heller et al. | 248/123.2 |
| 4,741,607 | 5/1988 | Heller | 248/123.2 X |
| 5,173,802 | 12/1992 | Heller | 359/384 |
| 5,186,422 | 2/1993 | Nakamura | 248/123.2 |
| 5,205,522 | 4/1993 | Nakamura | 248/123.11 |
| 5,480,114 | 1/1996 | Nakamura | 248/123.2 |
| 5,651,718 | 7/1997 | Nakamura | 248/280.11 X |
| 5,667,186 | 9/1997 | Luber et al. | 248/123.11 X |

FOREIGN PATENT DOCUMENTS

| 0 237 968 | 9/1987 | European Pat. Off. . |
| 0 628 290 A1 | 12/1994 | European Pat. Off. . |
| 0 656 194 A1 | 6/1995 | European Pat. Off. . |
| 43 20 443 A1 | 12/1994 | Germany . |

OTHER PUBLICATIONS

English Abstract of Japanese Patent Laid–Open Publication No. 269463/1994.

*Primary Examiner*—Derek J. Berger
*Attorney, Agent, or Firm*—Michael D. Bednarek; Crowell & Moring LLP

[57] ABSTRACT

The vertical movement of a retaining link mechanism and the horizontal movement of a counterweight are interlocked by a drive mechanism for balancing in weight between a medical optical device and/or its auxiliary devices and the counterweight about the center of pivot. Accordingly, the action of the drive mechanism makes a balance in the horizontal and vertical movements of the operating microscope combination, thereby automate the balancing control readily.

14 Claims, 6 Drawing Sheets

AUTOMATIC BALANCING MECHANISM FOR MEDICAL STAND APPARATUS

BACKGROUND OF THE INVENTION

1. Field of the Invention

The present invention relates to an automatic balancing mechanism for use with a medical stand apparatus, which is capable of advancing and holding heavy devices such as an operating microscope and its auxiliary devices at a desired spatial position during microsurgery.

2. Prior Art

Microsurgery is known particularly in the fields of brain surgery and cardiac surgery using a operating microscope as a "medical optical device" for viewing and inspecting a part to be treated during the operation. Various stand apparatuses are available for holding at a desired spatial position the heavy devices such as an operating microscope and its auxiliary devices. A typical type of the stand apparatus comprises a retaining link mechanism of parallel link pivotally (or tiltably) mounted at the middle to a support base, an operating microscope mounted to one end of the retaining link mechanism, and a counterweight mounted to the other end of the retaining link mechanism for countervailing the weight of the operating microscope relative to the pivot thereof In common, the stand apparatus of the balancing type is installed at an optimum position in an operation room depending on the content of the surgery to be carried out and balance adjustment is performed. The operating microscope is provided with various auxiliary devices including a side microscope for an assistant doctor and a video camera. The balance on the stand apparatus should be adjusted between the counterweight and the operating microscope with its auxiliary devices, with the counterweight shifted in accordance with the operating microscope and auxiliary devices if any.

It is essential for retaining the operating microscope and its auxiliary devices at a desired position in the space to balance in both the horizontal direction (when gravity acts vertically) and the vertical direction (when an imaginary direction where gravity acts horizontally). Otherwise, when the parallel link mechanism is biased, the weight balance will be lost and fail to retain the operating microscope at the desired spatial position. For making the balance, two counterweights are conventionally provided for controlling in both the vertical and horizontal directions respectively or one single counterweight is adjustably moved in both the vertical and horizontal directions. However, either manner would be realized by a complicated bulky system, which will be undesirable.

I, the inventor, developed an improved type of the stand apparatus in which a retaining link mechanism carrying a microscope and its auxiliary devices is arranged movable in the vertical direction while a counterweight is arranged movable in the horizontal direction so that the balance is held in both the vertical and horizontal directions (as is disclosed in Japanese Patent Laid-open Publication No. 269463/1994.

My previous invention is actually not so satisfactory because the balance is manually adjusted in spite of its simpler construction than that of any other prior art. The balancing adjustment will hardly be automated unless modified and thus neither simpler balance adjustment nor minimization of the involving time could be achieved.

The present invention is directed towards overcoming the above drawback and its object is to provide an automatic balancing mechanism for a medical stand apparatus capable of automatically balancing an optical device for medical use and its auxiliary devices.

SUMMARY OF THE INVENTION

For achievement of the foregoing object, a stand for supporting a medical optical device according to the present invention is arranged in which the vertical movement of a retaining link mechanism and the horizontal movement of a counterweight are interlockedly conducted by a drive mechanism for balancing in weight between the medical optical device and/or its auxiliary devices and the counterweight about the center of pivot. Accordingly, the control of the drive mechanism makes a balance in the horizontal and vertical movements of the medical optical device such as an operating microscope, and thereby automates the balancing control readily.

In the description of the invention, "the vertical movement" and "the horizontal movement" mean a vertical component and a horizontal component of the movement respectively but are not indicative in a strict sense of substantially a motion in the vertical direction or a motion in the horizontal direction of the retaining link mechanism or the counterweight.

The present invention is not limited to the above summary and its other objects, advantages, features, and applications will become more apparent from the following description in conjunction with the accompanying drawings. It should be understood that changes and modifications are possible without departing from the spirit and scope of the invention.

DESCRIPTION OF PREFERRED EMBODIMENT

Figure 1:
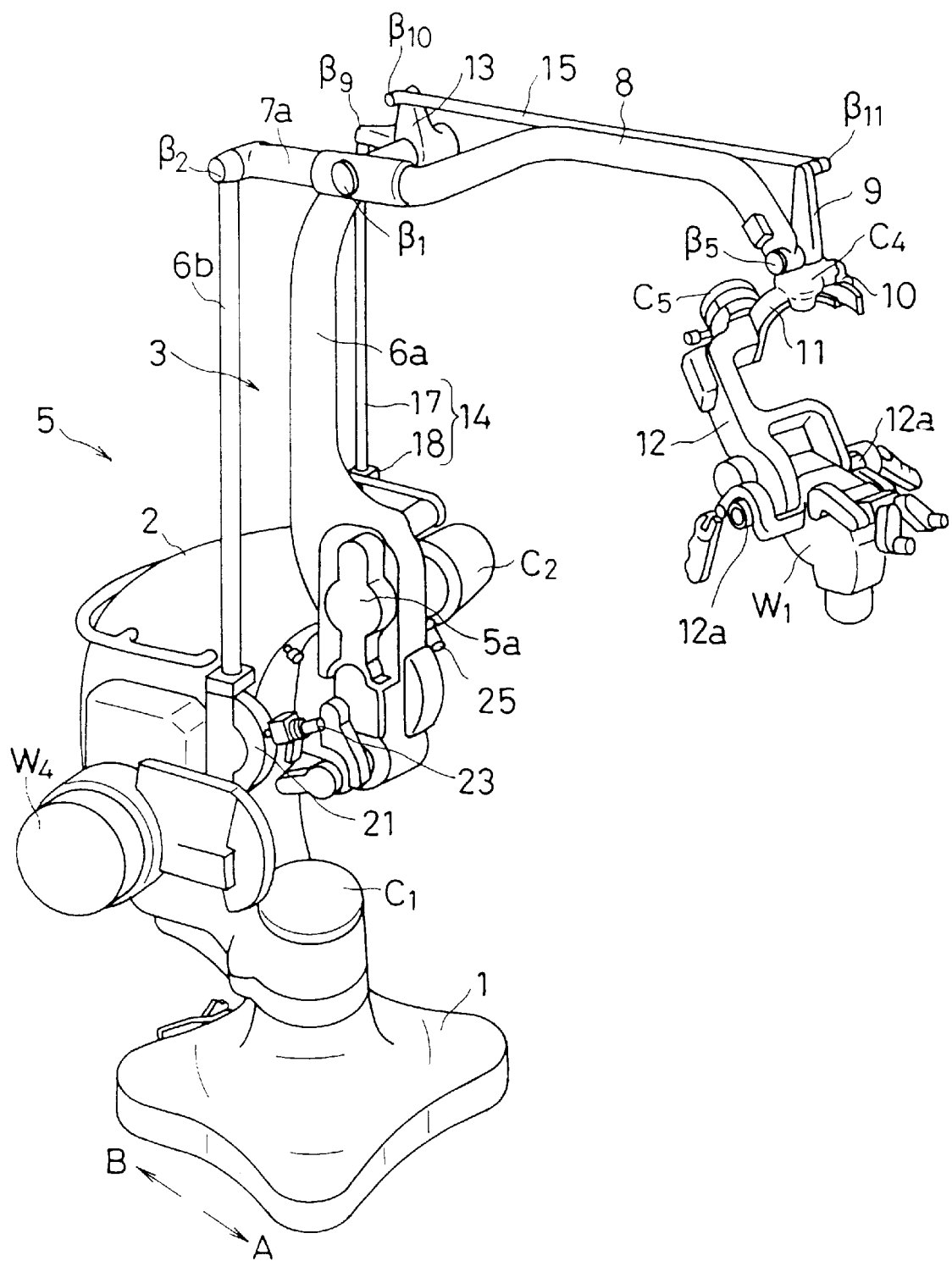
FIG. 1 is a perspective view of a medical stand apparatus showing one embodiment of the present invention.

A preferred embodiment of the present invention will be described in more details referring to the accompanying drawings. It should be noted that the front and rear directions are represented by A and B respectively throughout the drawings.

Denoted at 1 a base installed on the floor of an operation room. A swivel mount 2 which rotates about a vertical pivot axis $\alpha_1$ is mounted on the base 1. The rotation about the pivot axis $\alpha_1$ can be locked by the action of an electromagnetic clutch $C_1$. The mount 2 has a horizontal center pivot S supporting a middle part (5a) of a retaining link mechanism 5 which comprises a first parallel link assembly 3 and a second parallel link assembly 4. The retaining link mechanism 5 includes a group of three vertical arms 6a, 6b, and 6c and another group of three horizontal arms 7a, 7b, and 7c. The middle part 5a of the front vertical arm 6a of the retaining link mechanism 5 is pivotally joined to the horizontal center pivot S.

Figure 2:
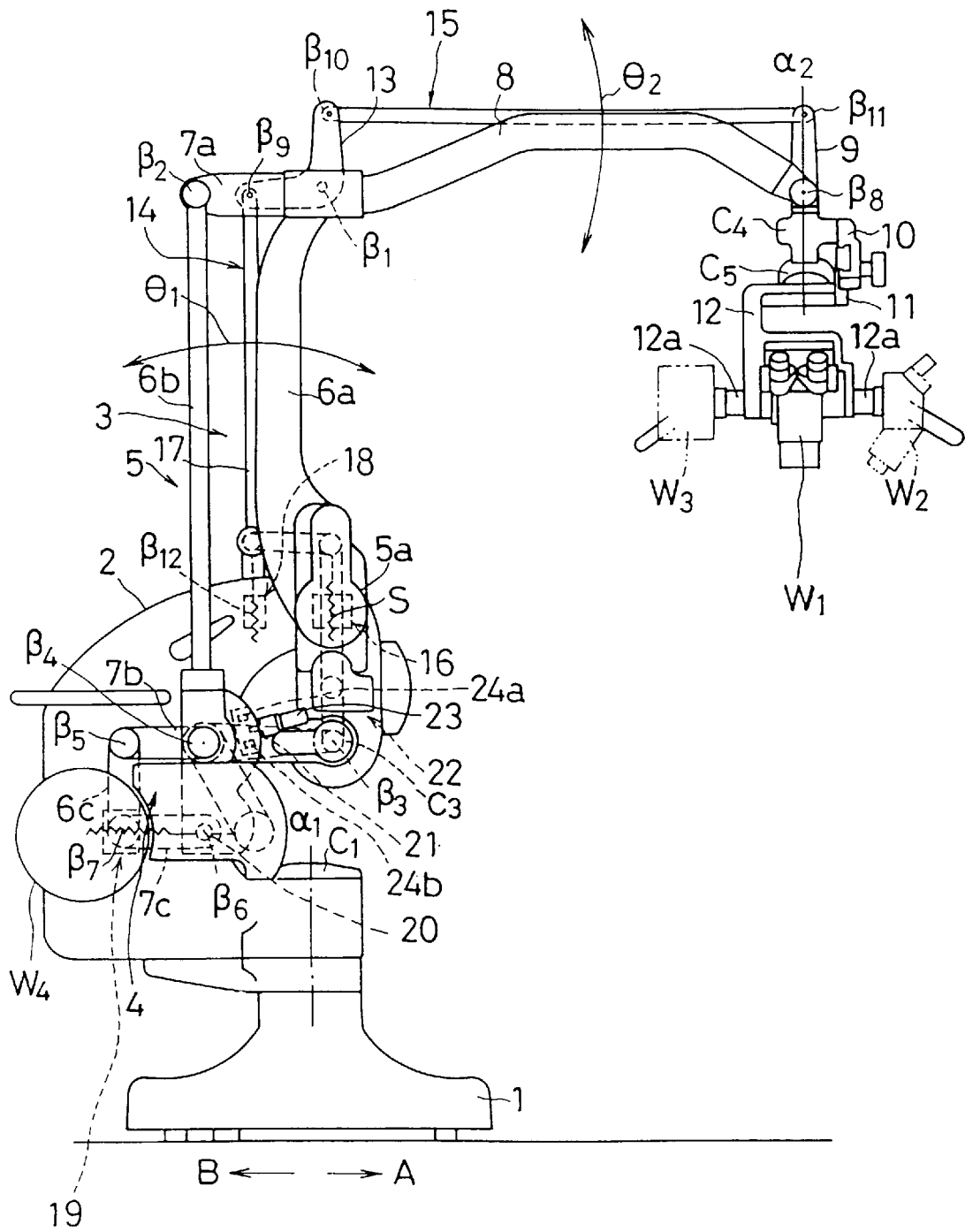
FIG. 2 is a side view of the medical stand apparatus.

The horizontal center pivot S is associated with an electromagnetic clutch $C_2$ (FIG. 3) which locks up the vertical arm 6a at a desired pivotal position (through a displacement $\theta_1$ in the crosswise directions of the retaining link mechanism 5, as shown in FIG. 2). The front vertical arm 6a pivotally joined to the horizontal center pivot S has an arcuate shape setting back rearwardly for free movement of a surgeon. The front vertical arm 6a is rather elaborate in its inner construction but acting as simply a member of the link assembly. The retaining link mechanism 5 is movable on seven joints $\beta_1$ to $\beta_7$ (FIG. 2) so that it can be shifted with the first and second parallel link assemblies 3,4 being in parallel respectively to form a parallelogram.

The upper horizontal arm 7a of the retaining link structure 5 is integrally joined by the joint $\beta_1$ to a jib arm 8 extending to the front. The jib arm 8 is pivotally joined at its distal end by a joint $\beta_8$ to a vertical front arm 9. The jib arm 8 is arranged of an arcuate shape setting back outwardly for clearing the head of a doctor and pivoted for vertical movement through $\theta_2$ (FIG. 2). The jib arm 8 can be locked at any desired angle through $\theta_2$ by the action of an electromagnetic clutch $C_3$ provided adjacent to the $\theta_3$.

The front arm 9 is joined at its lower end to a slider 10 which engages with an arcuate lever 11. The arcuate lever 11 is linked to a operating microscope $W_1$ (i.e. a medical optical device) by a holder frame 12 having substantially a fork-like shape. The slider 10 is rotatable about a pivot axis $\alpha_2$ and its rotation can be locked by the action of an electromagnetic clutch $C_4$. The holder frame 12 is also arranged rotatable about a pivot axis $\alpha_3$ and its rotation can be locked by the action of an electromagnetic clutch $C_5$. The holder frame 12 has a couple of interfaces 12a provided at both sides thereof for transmission of a light flux from the operating microscope $W_1$. Applicable auxiliary devices such as a side microscope $W_2$ for an assistant doctor and a video camera $W_3$ for records can detachably be mounted to the interfaces 12a. The weight of a holder assembly with the microscope $W_1$ is varied depending on the presence or absence of the auxiliary devices.

An L-shaped crank member 13 is attached to the joint $\beta_1$ as being the origin of the jib arm 8. The L-shaped crank member 13 has at the rear end a joint $\beta_9$ connected by a vertical sub-arm 14 to a joint $\beta_{12}$ on the mount 2 and at the upper end a joint $\beta_{10}$ connected by a horizontal sub-arm 15 to an upper joint $\beta_{11}$ of the front arm 9. More specifically, the crank member 13 is pivoted on the joint $\beta_1$ at the proximal end of the jib arm 8. In the crank member 13, a joint $\beta_9$ at the rear end is on a horizontal line from the joint $\beta_1$ and a joint $\beta_{10}$ at the upper end is on a vertical line from the joint $\beta_1$. The vertical sub-arm 14 connecting the rear joint $\beta_9$ of the crank member 13 to the joint $\beta_{12}$ on the mount 2 extends in parallel to the vertical arm 6a and has a length equal to the (vertical) distance between the joint $\beta_1$ and the center pivot S for the vertical arm 6a. The horizontal sub-arm 15 connecting the upper joint $\beta_{10}$ of the crank member 13 to the upper joint $\beta_{11}$ of the front arm 9 extends in parallel to and is identical in the (horizontal) length to the jib arm 8.

With the vertical sub-arm 14 and the horizontal sub-arm 15, two parallel link loops ($\beta_1 \rightarrow \beta_9 \rightarrow \beta_{12} \rightarrow S$) and ($\beta_1 \rightarrow \beta_8 \rightarrow \beta_{11} \rightarrow \beta_{10}$) are added. This allows the crank member 13 to remain not rotated in its position whenever the retaining link mechanism 5 (including the first and second parallel link assemblies 3,4) is shifted from one form to another. Accordingly, the front arm 9 is maintained in its position thus holding the operating microscope $W_1$ in the vertically downward direction.

The retaining link mechanism 5 is mounted by a vertical slide mechanism 16 (FIG. 4) to the mount 2 so that it can move upward and downward. The vertical slide mechanism 16 comprises a screw receiver 31 pivotally mounted on the center pivot S of the mount 2, and a screw $N_1$ threaded into the screw receiver $J_1$. The retaining link mechanism 5 is joined to the screw $N_1$ by a fixing means not shown. This allows the retaining link mechanism 5 to move upward and downward and turn about the center pivot S together with the screw $N_1$.

The vertical sub-arm 14 consists of an upper arm body 17 and a lower length adjusting mechanism 18. The length adjusting mechanism 18 comprises a screw receiver $J_2$ pivotally mounted on the joint $\beta_{12}$ and a screw $N_2$ threaded into the screw receiver $J_2$. The arm body 17 is linearly joined at the lower end to the screw $N_2$ by a fixing means not shown. This allows the vertical sub-arm 14 to be varied in the length by the length adjusting mechanism 18.

A counterweight $W_4$ is mounted in a horizontally moveable manner by a horizontal slide mechanism 19 to the horizontal arm 7c below the second parallel link assembly 4. The horizontal slide mechanism 19 comprises a screw receiver $J_3$ fixedly mounted to the counterweight $W_4$ and a screw $N_3$ extending along the horizontal arm 7c. The screw $N_3$ is longer than the horizontal arm 7b and coupled to a universal joint 20 at the end corresponding the front joint $\beta_6$ of the horizontal arm 7c. Accordingly, the screw $N_3$ can transmit torque when its angular position is changed about the universal joint 20.

A detecting means 21 for detecting a balance of the retaining link mechanism 5 is mounted on the joint $\beta_4$ which is movable in the second parallel link assembly 4. The detecting means 21 will be explained later in more details.

Figure 4:
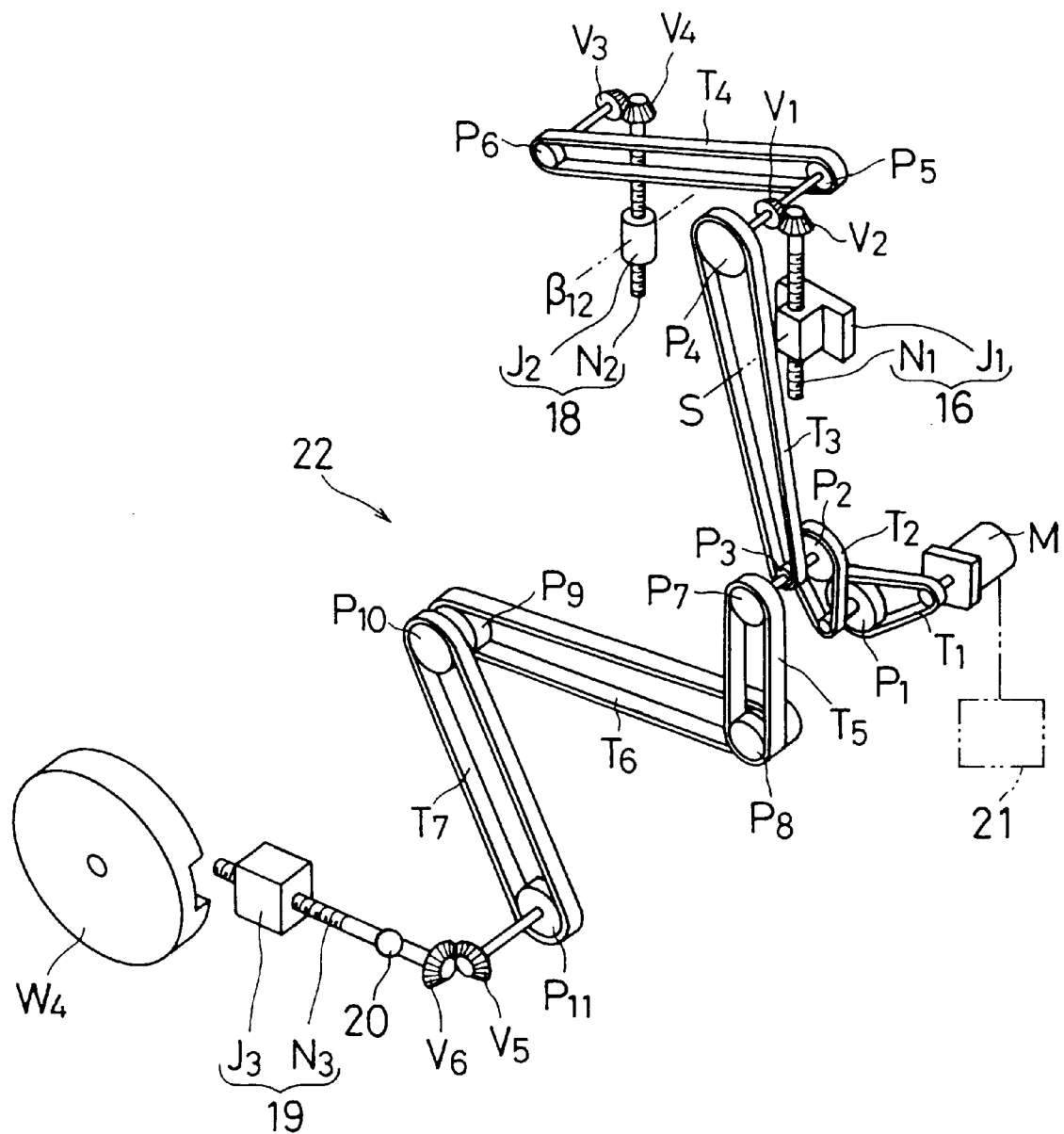
FIG. 4 is a perspective view of a drive mechanism.

As shown in FIG. 4, the vertical slide mechanism 16, the length adjusting mechanism 18, and the horizontal slide mechanism 19 are all connected to a drive mechanism 22 for movement relative to each other. The drive mechanism 22 is driven by a signal from the detecting means 21. The drive mechanism 22 comprises a power source or motor M, timing belts $T_1$ to $T_7$, timing pulleys $P_1$ to $P_{11}$, and bevel gears $V_1$ to $V_6$. The rotation of the motor M is transmitted via the three timing belts $T_1$ to $T_3$ and the four timing pulleys $P_1$ to $P_4$ to the bevel gear $V_1$ at the top. The bevel gear $V_1$ is meshed with the bevel gear $V_2$ mounted to the upper end of the screw $N_1$ of the vertical slide mechanism 16 so that the torque from the motor M can rotate the screw $N_1$. As the screw $N_1$ is rotated, it moves vertically relative to the screw receiver $J_1$ to cause the retaining link mechanism 5 anchored thereto to be lifted up and down about the center pivot S. The timing belts $T_1$ to $T_3$ and the timing pulleys $P_1$ to $P_4$ are used for transmission of the rotation of the motor M as they are advantageous for ease of the maintenance service. More particularly, any defective one of the timing belts $T_1$ to $T_3$ and the timing pulleys $P_1$ to $P_4$ can readily be repaired or replaced without interrupting the other parts.

The bevel gear $V_1$ is also connected via its axis to the timing pulley $P_5$ which transmits the rotation via the timing belt $T_4$ and the timing belt $P_6$ to the bevel gear $V_3$ located on the vertical sub-arm 14. The bevel gear $V_3$ is meshed with the bevel gear $V_4$ mounted to the upper end of the screw $N_2$ of the length adjusting mechanism 18, hence rotating the screw $N_2$. As the screw $N_2$ is rotated, it moves vertically relative to the screw receiver $J_2$ and causes the vertical sub-arm 14 to be varied in the length. The diameters of the timing pulleys $P_1$ to $P_6$ and the teeth of the bevel gears $V_1$ to $V_4$ are predetermined so that the adjusted length of the vertical sub-arm 14 is equal to the sliding distance of the retaining link mechanism 5.

Also, the timing pulley $P_2$ for transmission of the rotation both to the vertical slide mechanism 16 and to the length adjusting mechanism 18 is connected via its axis to the timing pulley $P_7$ of which torque is transmitted via the three timing belts $T_5$ to $T_7$ and the four timing pulleys $P_8$ to $P_{11}$ to the bevel gear $V_5$ at the bottom. The bevel gear $V_5$ is meshed with the bevel gear $V_6$ mounted to the distal end of the screw $N_3$ of the horizontal slide mechanism 19 to rotate the screw $N_3$. As the screw $N_3$ is rotated, it causes the screw receiver $J_3$ threaded therewith to be moved horizontally together with the counterweight $W_4$. The relation between the horizontal movement of the counterweight $W_4$ and the vertical movement of the retaining link mechanism 5 with the vertical sub-arm 14 will be explained later in more detail.

Figure 3:
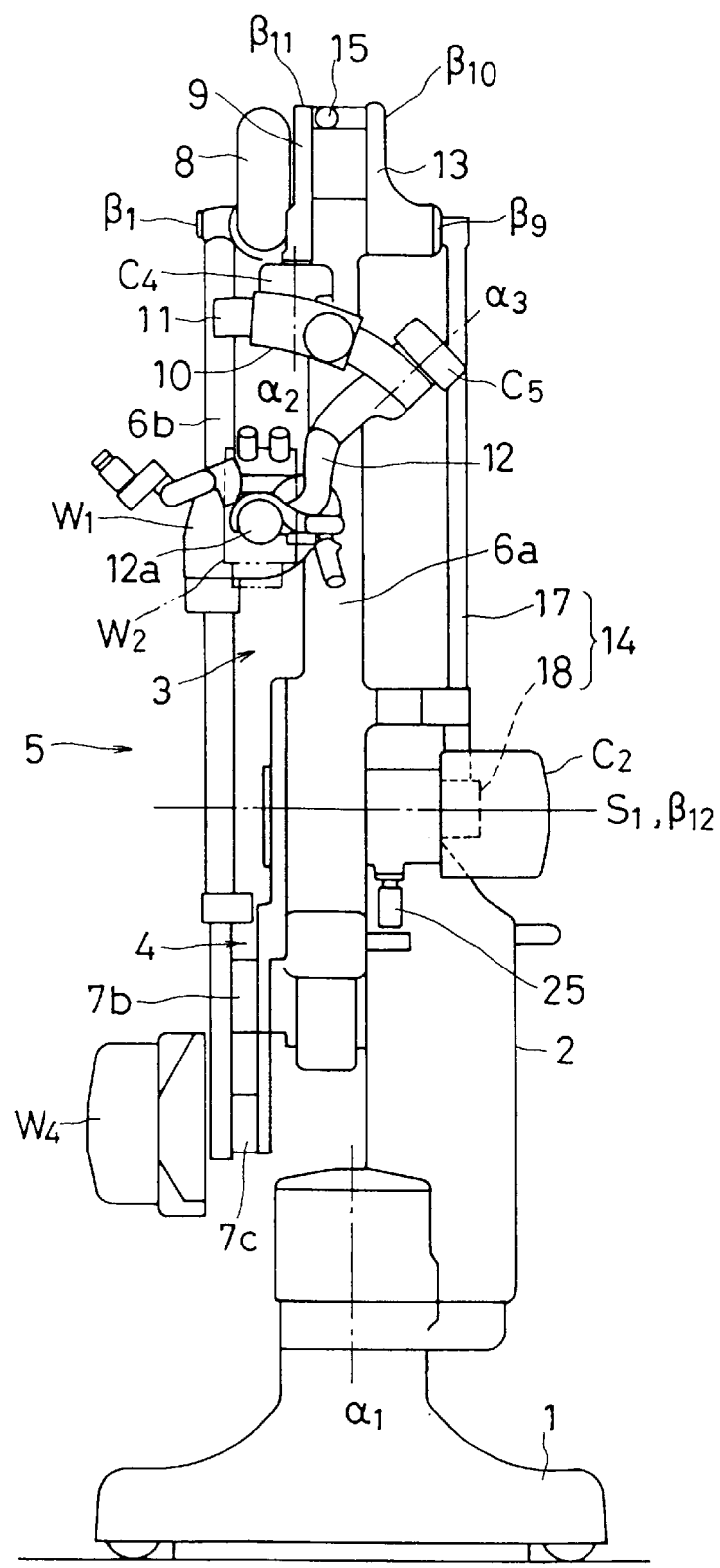
FIG. 3 is a front view of the medical stand apparatus.

The procedure of adjusting a balance on the stand apparatus will now be described. The procedure starts from a reference state in which the vertical arms 6a, 6b, and 6c and the horizontal arms 7a, 7b, and 7c are kept at their vertical and horizontal positions respectively (as shown in FIG. 2). The reference state is locked with a lock pin 23 partially inserted into the horizontal arm 7b near the joint $\beta_4$ of the vertical arm 6b. The lock pin 23 is loose-fitted for minimum freedom but securely positioned for maximum safety. Provided on both sides of the lock pin 23 are two switches 24a and 24b of the detecting means 21. If the lock pin 23 is dislocated to one side, the switch 24a or 24b at the side turns on to produce a signal for causing the motor M of the drive mechanism 22 to compensate the disposition. The center pivot S is also provided with a lock pin 25 for allowing no pivotal movement about the center pivot S (FIGS. 1 and 3).

Figure 6:
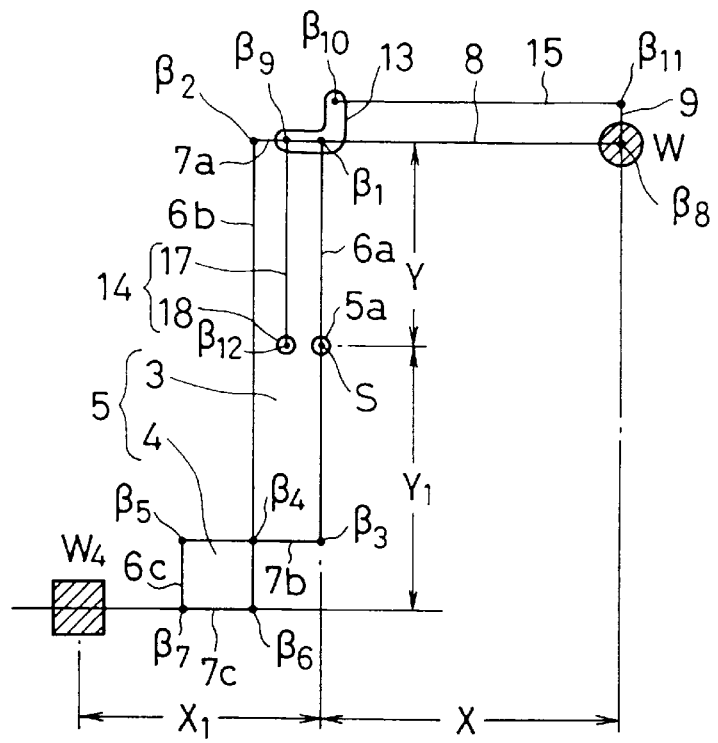
FIG. 6 is an explanatory view showing a balance between the total weight (W) of medical optical devices and the weight ($W_4$) of a counterweight.

The balancing action will be explained in more details referring to FIGS. 6 and 7. It is assumed that the operating microscope $W_1$, the side microscope $W_2$, and the video camera $W_3$ have been loaded onto the front end of the jib arm 8 and the total weight of their combination is expressed by $W(=W_1+W_2+W_3)$. To hold the operating microscope combination W at a desired position, the balance of the retaining link mechanism 5 has to be controlled both vertically and horizontally. Assuming that the vertical distance between the center pivot S and the operating microscope combination W is Y, the vertical distance between the center pivot S and the counterweight $W_4$ is $Y_1$ the horizontal distance between the center pivot S and the operating microscope combination W is X, and the horizontal distance between the center pivot S and the counterweight $W_4$ is $X_1$, the following equations should be established:

$W \times Y = W_4 \times Y_1$ for vertical balance, and $W \times X = W_4 \times X_1$ for horizontal balance.

Figure 5:
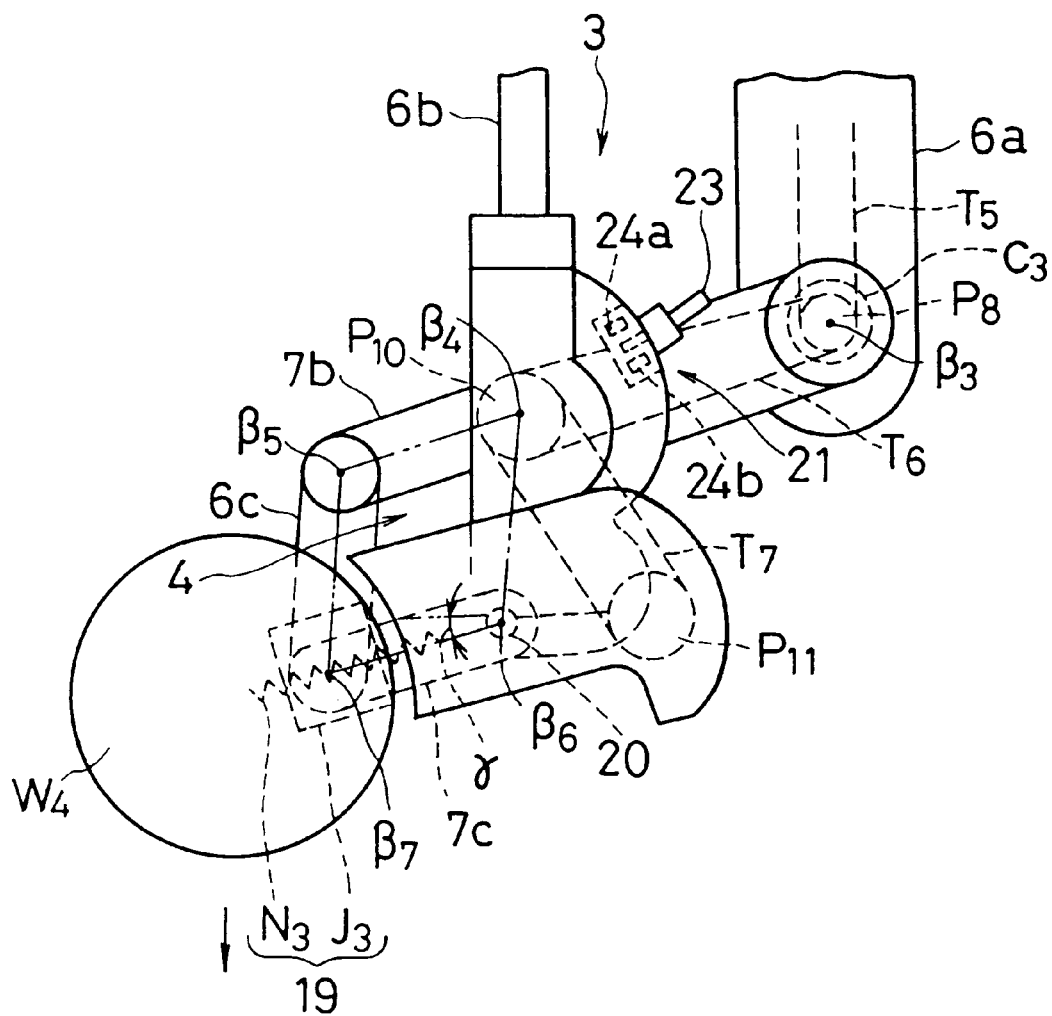
FIG. 5 is an enlarged side view showing a modification of a second parallel link assembly.

When the side microscope $W_2$ is removed off, the weight of the operating microscope combination loaded to the jib arm 8 shifts to $W-W_2$ which is smaller than that of the counterweight $W_4$. This will cause the second parallel link assembly 4 of the retaining link mechanism 5 to be tilted, for example, as shown in FIG. 5. However, the tilting movement upon the side microscope $W_2$ having been detached is eventually prevented by the action of the lock pin 23 which may only shake in the clearance. As the side microscope $W_2$ has been removed, the lock pin 23 is biased turning on one of the two switches of the detecting means 21, i.e. the switch 24b in this embodiment (FIG. 5). Upon being turned on, the switch 24b produces and delivers a signal to the drive mechanism 22 which in turn actuates the motor M for holding the lock pin 23 in its neutral position between the two switches 24a and 24b (i.e. making a balance). More specifically, the drive mechanism 22 moves the counterweight $W_4$ towards the operating microscope combination $W-W_2$ by a distance $X_2$ for producing a horizontal balance and drives the screw $N_1$ to lift up the retaining link mechanism 5 by a distance $Y_2$ for creating a vertical balance (while the vertical sub-arm 14 is also extended by an amount $Y_2$ by the action of the length adjusting mechanism 18). Accordingly, the center pivot S is lowered by $Y_2$ in relation to the retaining link mechanism 5 (FIG. 7).

The distances $X_2$ and $Y_2$ are expressed by:

$(W-W_2) \times (Y_1+Y_2) = W_4 \times (Y_1-Y_2)$ for vertical balance $(W-W_2) \times X = W_4 \times (X_1-X_2)$ for horizontal balance As the retaining link mechanism 5 and the counterweight $W_4$ have been displaced as described above, the operating microscope combination ($W-W_2$) is eventually balanced with the counterweight $W_4$ causing the lock pin 23 to stay in the neutral position between the two switches 24a and 24b. This is followed by the doctor pulling out the lock pin 23 (and the lock pin 25) to use the stand apparatus. The medical stand apparatus is being balanced on the center pivot S, allowing the operating microscope $W_1$ combination to be displaced vertically and horizontally to any desired position where it stays tightly as if in a non-gravity space. As the operating microscope combination is displaced to the desired position, it is locked up by the action of the electromagnetic clutches $C_1$ to $C_4$. The vertical sub-arm 14 is varied in the length corresponding to the vertical movement of the retaining link mechanism 5 and its function (of holding the operating microscope $W_1$ vertically in the downward direction regardless of the movement of the retaining link mechanism 5) will thus be guaranteed.

Also, the universal joint 20 is used at the joint $\beta_6$ of the screw $N_3$ in the horizontal slide mechanism 19 for the counterweight $W_4$. This allows the screw $N_3$ to be deflected at an angle $\gamma$ by the action of the universal joint 20 on the joint $\beta_6$ when the second parallel link assembly 4 is biased, as shown in FIG. 5, with the lock pin 23 removed. Accordingly, the screw $N_3$ is not affected by a local movement of the second parallel link assembly 4 at the joint $\beta_6$ but directly driven by the drive mechanism 22 for displacing the counterweight $W_4$. If the joint $\beta_6$ does not employ the universal joint 20, its movement causes an unwanted rotation of the screw $N_3$ thus interrupting the controlling action of the drive mechanism 22 and impairing the horizontal displacement of the counterweight $W_4$.

Figure 7:
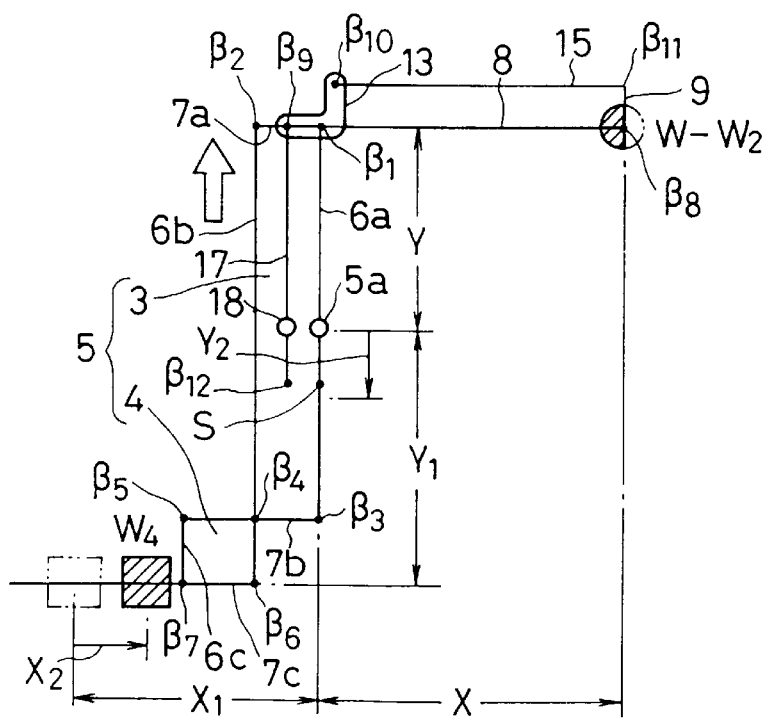
FIG. 7 is an explanatory view showing a balance between a reduced weight ($W-W_2$) of the medical optical devices and the counterweight ($W_4$).

Although the vertical distance $Y_2$ in the retaining link mechanism 5 appears as essentially great as the horizontal distance $X_2$ in FIG. 7, it is actually far smaller than $X_2$. This is because even small vertical movement can provide a sufficient balance adjusting effect in accordance with the movement of the whole retaining link mechanism 5. The vertical balance is expressed by $(W-W_2) \times (Y_1+Y_2) = W_4 \times (Y_1-Y_2)$ in which the distance $Y_2$ increases the difference between the left and right sides of the equation. The horizontal balance is expressed by $(W-W_2) \times X = W_4 \times (X_1-X_2)$ in which $X_2$ involves the right side of the equation. As apparent from the two equations, the small vertical movements in the retaining link mechanism 5 are sufficient for making a balance.

The above description is illustrative and not limited to the floor installation type of a medical stand in which the mount 2 is anchored to the floor. The mount 2 may be suspended from the ceiling of an operation room with equal success.

The auxiliary devices are not limited to the side microscope $W_2$ or the video camera $W_3$, and may include any other applicable instruments.

As set forth above, the present invention allows the vertical movement of the retaining link mechanism and the horizontal movement of the counterweight to be interlockedly conducted by the drive mechanism for balancing in weight between a medical optical device and/or its auxiliary devices and the counterweight about the center pivot point. Accordingly, the action of the drive mechanism creates a balance in the horizontal and vertical movements of the medical optical device such as a operating microscope, thereby automates the balancing control readily. In addition, the balance in the vertical direction is effected by biasing the retaining link mechanism and will be effectively adjusted with a small displacement of the retaining link mechanism.

What is claimed is:

1. A medical stand apparatus that includes an automatic balancing mechanism, the medical stand apparatus comprising:

a mount base having a center pivot;

a retaining link mechanism, the retaining link mechanism comprising: a first parallel link assembly and a second parallel link assembly cooperating with each other, and the retaining link mechanism being mounted to the center pivot of the mount base by a vertical slide mechanism for vertical movement of the retaining link mechanism;

a jib arm extending away from the first parallel link assembly, the jib arm having a distal end that extends away from the first parallel link assembly;

a medical optical device and/or its auxiliary devices mounted to the distal end of the jib arm; and a counterweight provided via a horizontal slide mechanism to a part of the second parallel link assembly in a horizontally moveable manner;

wherein the vertical movement of the retaining link mechanism and the horizontal movement of the counterweight are interlockedly driven by a drive mechanism so as to maintain balance between the counterweight and the weight of the medical optical device and/or its auxiliary devices.

2. A medical stand apparatus according to claim 1, wherein the vertical movement $Y_2$ of the retaining link mechanism and the horizontal movement $X_2$ of the counterweight are expressed by:

$$(W-W_2) \times (Y_1+Y_2) = W_4 \times (Y_1-Y_2) \text{ for vertical balance}$$
$$(W-W_2) \times X = W_4 \times (X_1-X_2) \text{ for horizontal balance}$$

in which W is the entire weight of medical optical devices including the medical optical device and/or its auxiliary devices, $W_2$ is a change in the weight of the medical optical devices (i.e., the negative change in the above equation), $W_4$ is the weight of the counterweight, Y is the vertical distance between the center pivot and the medical optical devices, $Y_1$ is the vertical distance between the center pivot and the counterweight, X is the horizontal distance between the center pivot and the medical optical devices, and $X_1$ is the horizontal distance between the center pivot and the counterweight.

3. A medical stand apparatus according to claim 1, further comprising a detecting means mounted to a movable portion of the retaining link mechanism for detecting a balanced state, wherein a signal which is transmitted from the detecting means to the drive mechanism for biasing the counterweight with the retaining link mechanism to maintain the balanced state.

4. A medical stand apparatus according to claim 1, wherein each of the first and second parallel link assembly comprises a combination of parallel extending vertical and horizontal arms, and wherein the first parallel link assembly includes an upper one of said horizontal arms that extends frontwardly to connect to the jib arm, and the counterweight is adapted for movement along the lower one of said horizontal arms of the second parallel link assembly.

5. A medical stand apparatus according to claim 4, further comprising:

a crank member pivotally mounted to a joint at a proximal end of the jib arm and having a rear end located on a horizontal line across the joint and an upper end located on a vertical line across the joint;

a vertical sub-arm which joins the rear end of the crank member and a part of the support base, extends in parallel with one of the vertical arms of the retaining link mechanism, and has a length equal to the distance between the upper joint of the one vertical arm and the center pivot;

a horizontal sub-arm joining the upper end of the crank member and the upper end of a front arm, the horizontal sub-arm extending in parallel with the jib arm, and having a length equal to that of the jib arm;

wherein a length adjusting mechanism is mounted to an intermediate portion of the vertical sub-arm for cooperating with the drive mechanism of the retaining link mechanism to change the length of the vertical sub-arm by a distance corresponding to the vertical movement of the retaining link mechanism.

6. A medical stand apparatus according to claim 4, wherein the horizontal slide mechanism comprises a screw receiver fixedly joined to the counterweight and a screw arranged in parallel to the lower horizontal arm of the second parallel link assembly, the screw arranged for being rotated by a driving force transmitted from the drive mechanism to move the counterweight and having a free movement joint located at the joint to the second parallel link assembly.

7. A medical stand apparatus according to claim 4, wherein the upper horizontal arm and the jib arm are integrally formed as a single piece.

8. A medical stand apparatus that includes an automatic balancing mechanism, the medical stand apparatus comprising:

a mount base having a center pivot;

a retaining link mechanism, the retaining link mechanism comprising:

a first parallel link assembly and a second parallel link assembly cooperating with each other, the retaining link mechanism being vertically slidably mounted to the center pivot of the mount base so as to allow vertical movement of the retaining link mechanism relative to the mount base;

a jib arm connected to the first parallel link assembly, the jib arm having a distal end that extends away from the first parallel link assembly;

a medical optical device and/or its auxiliary devices mounted to the distal end of the jib arm; and a counterweight that is slidably connected to a part of the second parallel link assembly so as to permit horizontal movement of the counterweight relative to the second parallel link assembly;

wherein the vertical movement of the retaining link mechanism and the horizontal movement of the counterweight are interlockedly driven by a drive mechanism so as to maintain a balance between the weight of the medical optical device and/or its auxiliary devices and the weight of the counterweight about the center pivot in both the vertical and horizontal directions.

9. The medical stand apparatus according to claim 8, wherein the vertical movement $Y_2$ of the retaining link mechanism and the horizontal movement $X_2$ of the counterweight are expressed by:

$$(W-W_2) \times (Y_1+Y_2) = W_4 \times (Y_1-Y_2) \text{ for vertical balance}$$

$$(W-W_2) \times X = W_4 \times (X_1-X_2) \text{ for horizontal balance}$$

in which W is the entire weight of medical optical devices including the medical optical device and/or its auxiliary devices, $W_2$ is a change in the weight of the medical optical devices (i.e. the negative change in the above equation), $W_4$ is the weight of the counterweight, Y is the vertical distance between the center pivot and the medical optical devices, $Y_1$ is the vertical distance between the center pivot and the counterweight, X is the horizontal distance between the center pivot and the medical optical devices, and $X_1$ is the horizontal distance between the center pivot and the counterweight.

10. The medical stand apparatus according to claim 8, further comprising a detecting means mounted to a movable portion of the retaining link mechanism for detecting when a balance exists between the weight of the medical optical device and/or its auxiliary devices and the weight of the counterweight about the center pivot in both the vertical and horizontal directions, a means for transmitting a signal from the detecting means to the drive mechanism for biasing the counterweight with the retaining link mechanism to maintain the balance between the weight of the medical optical device and/or its auxiliary devices and the weight of the counterweight about the center pivot in both the vertical and horizontal directions.

11. The medical stand apparatus according to claim 8, wherein each of the first and second parallel link assembly comprises a combination of parallel extending vertical and horizontal arms, the first parallel link assembly comprising an one of the upper horizontal arms that extends frontwardly to connect to the jib arm, and the counterweight is adapted for movement along a lower horizontal one of the arms of the second parallel link assembly.

12. The medical stand apparatus according to claim 11, further comprising:

a crank member pivotally mounted to an upper joint at a proximal end of the jib arm and having a rear end located on a horizontal line across the joint and an upper end located on a vertical line across the joint;

a vertical sub-arm which joins the rear end of the crank member and a part of the support base, the vertical sub-arm extending arms in parallel with one of the vertical arms of the retaining link mechanism, and has a length equal to the distance between the upper joint of the one vertical arm and the center pivot;

a horizontal sub-arm joining the upper end of the crank member and the upper end of a front arm, the horizontal sub-arm extending in parallel with the jib arm, and having a length equal to that of the jib arm;

wherein a length adjusting mechanism is mounted to an intermediate portion of the vertical sub-arm for cooperating with the drive mechanism of the retaining link mechanism to change the length of the vertical sub-arm by a distance corresponding to the vertical movement of the retaining link mechanism.

13. The medical stand apparatus according to claim 11, wherein the horizontal slide mechanism comprises a screw receiver fixedly joined to the counterweight and a screw arranged in parallel to the lower horizontal arm of the second parallel link assembly, the screw arranged for being rotated by a driving force transmitted from the drive mechanism to move the counterweight and having a free movement joint located a joint to the second parallel link assembly.

14. A medical stand apparatus according to claim 11, wherein the upper horizontal arm and the jib arm are integrally formed as a single piece.

* * * * *